United States Patent [19]

Gallati

[11] Patent Number: 4,683,197
[45] Date of Patent: Jul. 28, 1987

[54] DETECTION METHOD FOR OCCULT BLOOD

[75] Inventor: Harald Gallati, Dornach, Switzerland

[73] Assignee: Hoffmann-La Roche Inc., Nutley, N.J.

[21] Appl. No.: 730,605

[22] Filed: May 6, 1985

Related U.S. Application Data

[63] Continuation of Ser. No. 397,276, Jul. 12, 1982, abandoned.

[30] Foreign Application Priority Data

Jul. 16, 1981 [CH] Switzerland ................. 4673/81

[51] Int. Cl.⁴ .................. G01N 33/53; G01N 33/72; G01N 33/546
[52] U.S. Cl. .......................... 435/7; 436/66; 436/513; 436/518; 436/534; 436/541
[58] Field of Search ............ 435/7, 28; 436/66, 518, 436/534, 538, 513, 540, 541

[56] References Cited

U.S. PATENT DOCUMENTS

| | | | |
|---|---|---|---|
| 3,790,447 | 2/1974 | Hirata et al. | 435/7 |
| 4,134,792 | 1/1979 | Boguslaski et al. | 435/7 |
| 4,275,149 | 6/1981 | Litman et al. | 435/7 |
| 4,281,061 | 7/1981 | Zuk et al. | 435/7 |

FOREIGN PATENT DOCUMENTS

32782 7/1981 European Pat. Off. ............ 436/531

OTHER PUBLICATIONS

Songster et al, Cancer, 45: 1099-1102 (Mar. Supplement 1980).
Erman et al, Biochim. Biophys. Acta, 393: 343-349 (1975).

Primary Examiner—Esther M. Kepplinger
Attorney, Agent, or Firm—Jon S. Saxe; George M. Gould; Julie M. Prlina

[57] ABSTRACT

A method for the detection of occult human blood in human stool samples by immunologically determining after performing the known peroxidase procedure, a human component abnormally present in the stool.

10 Claims, No Drawings

DETECTION METHOD FOR OCCULT BLOOD

This is a continuation of application Ser. No. 397,276 filed July 12, 1982, abandoned.

BACKGROUND OF THE INVENTION

The detection of occult blood in the stool is a recognized method for the early diagnosis of carcinomas of the colon. The chemical detection of occult blood in the stool is an old, tried and simple method of investigation. In this case, the principle of the test if based on the peroxidase action of hemoglobin, whereby, in the presence of hydrogen peroxide, an indicator such as benzidine, o-toluidine or guaiacum is oxidized and a blue coloration results. This is, of course, a non-specific reaction, since besides hemoglobin other stool components such as food, primarily blood sausage, red meat as well as vegetable constituents, and intestinal bacteria also have peroxidase activity.

There are, for example, commercialized tests available for the detection of occult blood in the stool. An example of such test is the "Colo-Rectal-Roche-Test ®" made available by Hoffmann-La Roche AG Diagnostica. This test is available in the form of test envelops having defined test fields to which a sample of stool is added. The paper covering the test field is impregnated with guaiacum which acts as redox indicator. The application of an ethanol hydrogen peroxide solution will dissolve the water insoluble guaiacum and start the peroxidation reaction with the hemoglobin of the sample to provide a blue color.

In the commercialized tests for the detection of occult blood in the stool, which are available in the form of test envelopes, the patient is requested as a precaution to give up the consumption of raw and semi-raw meat as well as of sausages (e.g. tartare, steak, liver, salami, blood sausage) for three days before the beginning of the test and during the period of the test.

This and other precautions are troublesome for the patients and are not entirely capable of excluding false positive results, which necessitate time-consuming and expensive subsequent investigations such as coloscopy or rectoscopy.

For this reason it has also been proposed (Songster, C. L. et al. in American Cancer Society 1099 et seq., 1980), in the case of a conventional test envelope impregnated with guaiacum, to use an additional stool sample reception site which is not impregnated with guaiacum and, in the case of a positive guaiacum sample, to investigate the content of this additional stool sample reception site for the presence of human hemoglobin with the aid of an immunological method.

This procedure has a disadvantage in that this additional stool sample is not absolutely identical with the stool samples which are subjected to the guaiacum test; for example, the additional stool sample has been removed from another stool evacuation or from another part of the stool, which again can lead to uncertainties.

There accordingly exists a need to investigate stool samples, which have been subjected to the peroxidase test, for the presence of components of human origin which are not normally present in human stool and which would interfere with an accurate determination of the occult blood by the peroxidase test.

Since the peroxidative test or method is carried out with the aid of an ethanolic solution, there has hitherto been the opinion that this method destroys the immunological properties of components of human origin which are not normally present in human stool.

SUMMARY OF THE INVENTION

The invention relates to a method for detection of occult human blood in a human stool sample. The sample has been subjected to a peroxidase test whereby the peroxidative activity of hemoglobin in the presence of alcoholic hydrogen peroxide oxidizes a redox indicator. Thereafter an immunologically detectable component which is of human origin but which is normally absent (not normally present) in human stool is detected immunologically. Such a component may be selected from the group consisting of human hemoglobin, human albumin and human globulin.

It was surprisingly found in the scope of the present invention that it is readily possible to carry out on a stool sample, which has previously been subjected to the peroxidase test, an immunological detection for components of human origin which are normally absent (not normally present) in human stool.

DETAILED DESCRIPTION OF THE INVENTION

The present invention is concerned with a method for the detection of occult human blood in human stool samples according to the peroxidase test, which method comprises, after having carried out the peroxidase test, immunologically detecting in the same stool sample an immunologically detectable component of human origin which is normally absent (not normally present) in human stool.

As used herein occult human blood in human stool refers broadly to human blood in human stool, which blood may be in amounts so small as not to be readily detectable by the naked eye.

As already mentioned, there come into consideration in the case of the peroxidase test those tests or methods or procedures known per se for use in determining if a stool sample contains blood. Where a stool sample contains blood the peroxidative activity of hemoglobin in the presence of an alcoholic hydrogen peroxide solution will oxidize the redox indicator. As examples of redox indicator used in the peroxidase test there come to mind benzidine, o-toluidine or guaicum.

The hydrogen peroxide used in the peroxidase test may be made up in any art recognized alcohol solution capable of carrying out the peroxidase test. Typically the peroxidase test is carried out with the aid of an ethanolic hydrogen peroxide solution.

As immunologically detectable components of human origin to be determined, in the stool sample, which components are normally absent (not normally present) in human stool, there are included, for example, human hemoglobin, human albumin or human globulin. As to the human globulin there is included, for example, immunoglobulin G. immunoglobulin M or immunoglobulin A.

The immunological detection of the immunologically detectable components can be carried out according to any immunological method which is known in immunology. The sandwich method has been found to be an especially preferred method. In this method the component to be detected, i.e. the immunologically detectable component, is determined with the aid of two specific antibodies, of which one is bound to a solid phase and the other is provided with a label. The antibodies used can be obtained from different animal serum, but various monoclonal antibodies can be used. The solid phase may by any art recognized solid phase for immunological assays. The preferred solid phase is synthetic solid phase material known per se, such as polyvinyl fluoride, polyethylene glycols, polystyrene, and the like. Beads as known per se in immunology of synthetic material have been shown to be especially suitable as the solid phase. The labeled antibody may be labeled by any labeling means known in immunology, although enzymes are especially suitable. Peroxidase is preferably used as the enzyme.

The immunological detection of these components can, however, also be carried out using a latex agglutination test.

The following Examples further illustrate the invention but are not meant to limit the invention in scope or spirit.

EXAMPLE 1

Human stool is treated with 0 ml, 1 ml, 2 ml, 4 ml, 8 ml and 16 ml of human blood per 100 g of fresh stool and homogenized. A spatula tip of each of these stool samples is placed in the two compartments of a test envelope "Colo-Rectal-Roche-Test ®" which is commercially available from Hoffmann-La Roche AG Diagnostica). The envelopes are sealed and stored at room temperature for two days.

In order to detect occult blood in the stool, the flap "Only to be opened by the physician" is removed and then firstly one drop of a solution of 0.1M citrate buffer with 20% ethanol (pH 5) and subsequently one drop of a 3% $H_2O_2$ solution in ethanol are added to the stool sample and after 30 seconds the resulting colour intensity (0 to 4+) is estimated.

For the subsequent enzyme-immunological detection of human globulin in the stool, there is cut out from the test envelope a 9 mm wide strip containing the two stool stains and this strip is incubated at 37° C. in 5 ml of 0.1M $NaHCO_3$ of pH 9.5 for 30 minutes. After mixing well, 0.1 ml of the clear, odourless, brown-yellow coloured extract is then pipetted into a synthetic test tube ($\phi=1$ cm), 0.1 ml of 0.2M sodium phosphate buffer of pH 6.5 is admixed, a polystyrene bead ($\phi=6.35$ mm) sensitized with (sheep)anti-humanglobulin is added and the mixture is incubated at 37° C. for 1 hour. After separating the unbound material, the bead is again incubated at 37° C. for 1 hour with 0.2 ml of (goat)anti-human-globulin-peroxidase, dissolved in 0.2M sodium phosphate buffer of pH 6.5 with 20% goat serum and 2 g/l of bovine serum albumin. After three-fold washing with distilled water, the bead is incubated for 30 minutes at room temperature in 0.5 ml of substrate buffer (0.1M citrate buffer of pH 5.0 with 6 mM of $H_2O_2$ and 40 mM of o-phenylenediamine) in order to detect the immunologically bound peroxidase. After stopping the enzymatic reaction by adding 2 ml of a 1N HCl, the absorption difference at the wavelength 492 nm ($\Delta A_{492\ nm/RT/30\ min.}$) is determined photometrically in order to ascertain the content of human globulin. The results are compiled in Table I.

TABLE 1

| Test envelope | Occult blood test (Colour intensity) | Enzyme-immunological test ($\Delta A_{492\ nm/RT/30\ min.}$) |
|---|---|---|
| Without stool sample (reagent blank value) | 0 | 0.000 |
| Stool sample without human blood | 0 | 0.080 |
| Stool sample with 1 ml of human blood per 100 g of stool | 0 | 0.300 |
| Stool sample with 2 ml of human blood per 100 g of stool | 0 | 0.410 |
| Stool sample with 4 ml of human blood per 100 g of stool | 2+ | 0.680 |
| Stool sample with 8 ml of human blood per 100 g of stool | 4+ | 0.950 |
| Stool sample with 16 ml of human blood per 100 g of stool | 4+ | 1.530 |

The sensitivity of the enzyme-immunological occult blood test is evident from Table I, since the absorption difference increases significantly dependent on the concentration of human blood.

EXAMPLE 2

Human stool is treated with in each case 4 ml of (a) human blood, (b) goat blood, (c) bovine blood, (d) rabbit blood, (e) horse blood as well as with 10 mg of horesradish peroxidase per 100 g of fresh stool and homogenized. A spatula tip of each of these stool samples is placed in the two compartments of the test envelope "Colo-Rectal-Roche-test ®", the envelopes are sealed and stored at room temperature for one day.

In order to detect occult blood in the stool, the flap "Only to be opened by the physician" is removed and firstly one drop of a solution of 0.1M citrate buffer with 20% ethanol (pH 5) and subsequently one drop of a 3% $H_2O_2$ solution in ethanol are added to the stool sample and after 30 seconds the resulting colour intensity (0 to 4+) is estimated.

For the subsequent enzyme-immunological detection of human globulin in the stood samples, there is cut out from the test envelopes a 9 mm wide strip containing the two stool stains and this strip is incubated at 37° C. in 5 ml of 0.1M $NaHCO_3$ of pH 9.5 for 30 minutes. After mixing well, 0.1 ml of the clear, red-brown coloured extract is pipetted into a test tube, 0.1 ml of 0.2M sodium phosphate buffer of pH 6.5 is admixed, a polystyrene bead sensitized with (sheep) anti-human globulin is added and the mixture is incubated at 37° C. for 1 hour. After separating the unbound material, the bead is incubated at 37° C. for 1 hour with (goat)anti-human-globulin-peroxidase, dissolved in 0.2M sodium phosphate buffer of pH 6.5 with 20% goat serum and 2 g/l of bovine serum albumin. The unbound material is separated, the bead is washed three times with distilled water and subsequently, for the quantitative determination of the immunologically-bound peroxidase, incubated at room temperature for 30 minutes in 0.5 ml of substrate buffer (0.1M citrate buffer of pH 5.0 with 6 mM of $H_2O_2$ and 40 mM of o-phenylenediamine). After stopping the enzymatic reaction by adding 2 ml of a 1N HCL, the absorption difference at the wavelength 492 nm is determined photometrically in order to ascertain the content of human globulin. The results are compiled in Table II.

TABLE 2

| Test envelope | Occult blood test (Colour intensity) | Enzyme-immunological test ($\Delta A_{492}$ nm/RT/30 min.) |
| --- | --- | --- |
| Without stool sample (reagent blank value) | 0 | 0.000 |
| Stool sample without blood addition | 0 | 0.070 |
| Stool sample with 4 ml of human blood/100 g of stool | 2+ | 0.650 |
| Stool sample with 4 ml of goat blood/100 g of stool | 2+ | 0.050 |
| Stool sample with 4 ml of horse blood/100 g of stool | 2− | 0.080 |
| Stool sample with 4 ml of rabbit blood/100 g of stool | 2+ | 0.080 |
| Stool sample with 4 ml of bovine blood/100 g of stool | 2+ | 0.110 |
| Stool sample with 10 mg of peroxidase/100 g of stool | 4+ | 0.050 |

The specificity of the enzyme-immunological occult blood test is evident from Table II, since only samples containing human blood show a significant increase in the absorption difference, whereas samples containing animal blood or with peroxidase (but without human blood) show no such increase, but yet show a colour intensity.

What is claimed is:

1. A method for detection of occult human blood in a human stool sample comprising the steps of:
   (a) subjecting said sample to a peroxidase test whereby the peroxidative activity of hemoglobin in the presence of alcoholic hydrogen peroxide oxidizes a redox indicator, and
   (b) subsequently immunologically detecting in the same sample an immunologically detectable component of human origin selected from the group consisting of albumin and globulin.

2. A method according to claim 1 wherein the redox indicator is selected from the group consisting of benzidine, o-toluidine and guaiacum.

3. A method according to claim 1 wherein the alcoholic hydrogen peroxide in ethanolic hydrogen peroxide.

4. A method according to claim 1 wherein the immunologically detectable component of human origin is human albumin.

5. A method according to claim 4 wherein the human globulin is selected from the group consisting of immunoglobulin G, immunoglobulin M and immunoglobulin A.

6. A method according to claim 1 wherein the immunologically detectable component is immunologically detected in an immunological sandwich assay.

7. A method according to claim 6 wherein the immunological sandwich assay is carried out with two specific and different antibodies, obtained by immunizing two different animals, one of said antibodies being bound to a solid phase and the other having a label to provide a labelled antibody.

8. A method according to claim 7 wherein the solid phase is a synthetic bead.

9. A method according to claim 7 wherein the labelled antibody is labelled with an enzyme.

10. A method according to claim 9 wherein the enzyme is peroxidase.

* * * * *